United States Patent [19]

Adams

[11] Patent Number: 5,601,607
[45] Date of Patent: Feb. 11, 1997

[54] IMPLANTABLE CARDIOVERTER DEFIBRILLATOR HOUSING PLATED ELECTRODE

[75] Inventor: Theodore P. Adams, Edina, Minn.

[73] Assignee: Angeion Corporation, Plymouth, Minn.

[21] Appl. No.: 376,805

[22] Filed: Jan. 23, 1995

Related U.S. Application Data

[60] Continuation-in-part of Ser. No. 321,782, Oct. 12, 1994, Pat. No. 5,447,521, which is a division of Ser. No. 854,862, Mar. 19, 1992, Pat. No. 5,376,103.

[51] Int. Cl.⁶ .................................................. A61N 1/39
[52] U.S. Cl. .......................... 607/5; 607/36; 607/119
[58] Field of Search ................... 607/5, 4, 36, 116, 607/119, 121

[56] References Cited

U.S. PATENT DOCUMENTS

| | | | |
|---|---|---|---|
| 4,440,178 | 4/1984 | Bussard et al. | 607/121 |
| 4,502,492 | 3/1985 | Bornzin | 607/121 |
| 4,708,145 | 11/1987 | Tacker, Jr. et al. | 607/5 |
| 4,727,877 | 3/1988 | Kallok | 607/5 |
| 5,014,696 | 5/1991 | Mehra | 607/5 |
| 5,074,313 | 12/1991 | Dahl et al. | 607/119 |
| 5,107,834 | 4/1992 | Ideker et al. | 607/5 |
| 5,178,957 | 1/1993 | Kolpe et al. | 428/458 |
| 5,209,229 | 5/1993 | Gilli | 607/5 |
| 5,360,442 | 11/1994 | Dahl et al. | 607/119 |
| 5,376,103 | 12/1994 | Anderson et al. | 607/5 |

OTHER PUBLICATIONS

Guyton et al., "Capacitor Electrode Stimulates Nerve or Muscle without Oxidation–Reduction Reactions," Science, vol. 181, pp. 74–76, 607/121.

Primary Examiner—William E. Kamm
Assistant Examiner—Kennedy J. Schaetzle
Attorney, Agent, or Firm—Brad D. Pedersen

[57] ABSTRACT

A defibrillator for pectoral implant in a patient wherein the metal housing or case of the defibrillator is utilized as an electrode and is operative to supply electrical pulses. The housing is coated with an oxidation resistant material to optimize electrode function.

11 Claims, 9 Drawing Sheets

| PATTERN NUMBER | ELECTRODES AND POLARITIES | | |
|---|---|---|---|
| | RVA | SVC | CAN |
| 1 | − | + | + |
| 2 | − | 0 | + |
| 3 | + | − | − |
| 4 | + | 0 | − |

| PATTERN NUMBER | ELECTRODES AND POLARITIES | | |
|---|---|---|---|
| 5 | 0 | + | − |
| 6 | 0 | − | + |

| | |
|---|---|
| 1 | 2 |
| 1 | 4 |
| 1 | 5 |
| 1 | 6 |
| 2 | 1 |
| 2 | 3 |
| 2 | 5 |
| 2 | 6 |
| 3 | 2 |
| 3 | 4 |
| 3 | 5 |
| 3 | 6 |
| 4 | 1 |
| 4 | 3 |
| 4 | 5 |
| 4 | 6 |
| 5 | 1 |
| 5 | 2 |
| 5 | 3 |
| 5 | 4 |
| 6 | 1 |
| 6 | 2 |
| 6 | 3 |
| 6 | 4 |

| PATTERN NUMBER | ELECTRODES AND POLARITIES | | | |
|---|---|---|---|---|
| | RVA | SVC | CAN | SUB |
| 1 | − | + | + | + |
| 2 | − | + | − | − |
| 3 | + | − | − | − |
| 4 | + | − | + | + |

| PATTERN NUMBER | ELECTRODES AND POLARITIES | | | |
|---|---|---|---|---|
| 5 | 0 | − | + | + |
| 6 | 0 | + | − | − |

FIG. 18

IMPLANTABLE CARDIOVERTER DEFIBRILLATOR HOUSING PLATED ELECTRODE

CROSS-REFERENCE TO RELATED APPLICATIONS

This application is a continuation in part of U.S. patent application Ser. No. 08/321,782, filed Oct. 12, 1994, now U.S. Pat. 5,447,521, which is division of Ser. No. 854,862, filed Mar. 19, 1992, now U.S. Pat. No. 5,376,103, both of which are incorporated herein by reference.

BACKGROUND OF THE INVENTION

1. Field of the Invention

This invention relates to implantable cardioverter defibrillator (ICD) systems, and particularly to the electrodes and pulse generators thereof. The invention provides optimal materials for constructing pulse generator housings for use as an electrode.

2. Description of the Prior Art

The departure of the heart from normal action to uncoordinated and ineffectual contractions, "fibrillation," can lead to death within minutes unless corrected. One method of treatment to restore the normal heart action involves passing electrical current through the heart muscle. The effectiveness of such treatment is dependent on a number of factors, including the location of the electrodes used to apply the electrical current, the shape of the electrodes, and the magnitude, timing, and waveform of the current. While all these factors are significant, a fundamental problem of all such electrical treatments arises from tile fact that they all require large currents to accomplish defibrillation. And, because the heart muscle typically presents an electrical impedance in tile range of 40 to 100 ohms, signal amplitudes of several hundred volts are required to obtain the necessary current. The requirements for relatively high voltage and several-ampere currents combine to place great importance on efficient, low-resistance electrode arrangements for delivering tile defibrillation signal to the heart. Ideally the electrode would have no resistance itself and would be placed directly against the heart muscle to avoid the voltage drop across the tissue that surrounds the heart.

Various approaches to the optimal electrode, implanted in the body, have been attempted. For example, tile epicardial-patch electrodes comprise conductive and relatively large-surface area elements stitched directly onto the exterior of the heart. While this approach is satisfactory from an electrical standpoint, the attachment of the electrodes requires a major surgical procedure.

Another approach, the transvenous technique, utilizes a conducting filament threaded through an opening in a vein, and into the heart interior. When the filament coils up in a heart chamber, ideally against the chamber wall, a relatively large-area contact to tile cardiac muscle can be made. This approach requires that two such electrodes be used, one in the right-atrium (RA) position or in the nearby superior vena cava (SVC) position, and the other placed at the right-ventricular-apex (RVA) position. Despite the fact that transvenous electrodes can be inserted with a relatively simple surgical procedure, they have a serious shortcoming. Because of the design constraints that permit them to be threaded through the blood vessels, they cannot be depended upon to make adequate contact with the interior wall of the heart, and therefore they sometimes do not direct adequate current through a sufficient portion of the heart-muscle volume to achieve defibrillation.

Figures 1, 2, 3:
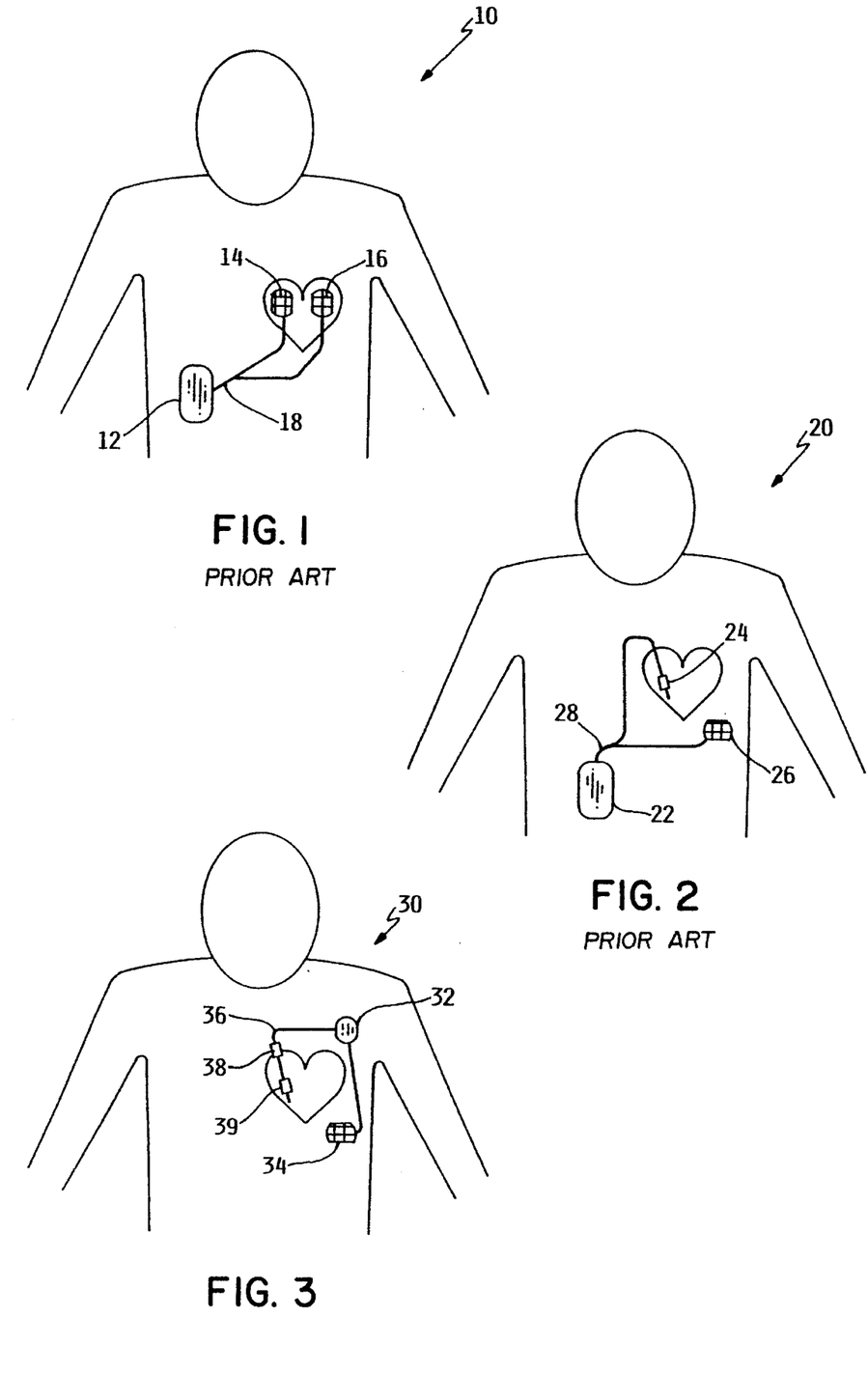
FIG. 1 illustrates a schematic representation of a defibrillating system of the prior art implanted in the abdominal cavity, and having epicardial-patch electrodes attached directly to tile heart.
FIG. 2 illustrates a schematic representation of a defibrillating system of the prior art having one transvenous electrode and one subcutaneous-patch electrode.
FIG. 3 illustrates a schematic representation of a defibrillating system of the present invention having a SVC electrode, an RVA electrode and one subcutaneous-patch electrode.

Another option is to combine a transvenous electrode with a subcutaneous patch (SUB). This approach implants a shallow, just-under-the-skin conductive element of appreciable area on the patient's left side to serve as an electrode, as illustrated in FIG. 2. Since the patch is not directly on the heart, current must pass through the intervening body tissue and fluid to reach the heart. The resistance of the intervening tissue and fluid requires the application of a higher voltage to achieve the desired current through the heart muscle, and the passage of tile current through the intervening material may lead to patient discomfort. Additionally, while the surgical procedure for implanting the subcutaneous patch is relatively minor compared to that required for implantation of electrodes directly against the heart muscle, it still presents some risk to the patient. Although the subcutaneous-patch approach provides the advantage of simpler and less risky surgery, the proximity of a subcutaneous patch to the body's surface leaves the electrode relatively unprotected, and as a result, such electrodes have been subject to flexure and breakage from mishaps, and even from normal body motions.

A final option is to utilize the pulse generator itself as an electrode. Because of the relatively high voltage and substantial currents involved in treatment, the size and weight of an implanted pulse generator (PG) is an important factor in defibrillation. The package or outer shell of the PG is usually a sealed housing made of titanium, selected for its relatively light weight and corrosion resistance. The weight of the PG is normally in excess of 200 grams, or approximately one half pound. The patient abdominal cavity is normally the chosen implantation site for space and comfort reasons. However, implantation of tile PG nearer the heart, for example in the pectoral region, provides the advantage of a more efficient system which in mm allows the size of the PG to be reduced. PG implantation near the heart also permits use of the metallic PG housing as an electrode, also called a "Can". This is, in a sense, a "free" electrode in that the housing is required in any case. Implanting the PG pectorally involves surgery little more invasive than that required to implant a subcutaneous patch. Furthermore, it eliminates the troublesome requirement for tunneling wires under the skin that accompanies the subcutaneous patch. and the PG is also not subject to crumbling and breakage. It is possible to use the PG enclosure as an electrode in combination with electrodes of the prior art, such as the RVA, SVC and subcutaneous-patch (SUB) electrodes. This facilitates the use of sequential defibrillation pulses having different spatial axes, demonstrated in the prior art to reduce the amount of energy needed for defibrillation (i.e. lower defibrillation threshold). Energy consumption is a vital concern since it is directly related to size and therefore also implantability.

Known "active can" electrode designs have been found to be less than optimal due to oxidation of the can material. Insofar as is known, no device has been made or proposed which solves this problem as applicant has.

SUMMARY OF THE INVENTION

The invention provides system and electrode design that is more reliable and more efficient than those of the prior art. The present invention involves optimizing the material used in tile pulse generator housing to improve its function as an electrode in the defibrillator system.

DESCRIPTION OF THE PREFERRED EMBODIMENTS

Recent developments in defibrillator, electrode and lead designs have demonstrated that lower defibrillation thresholds are achievable with transvenous leads where the ICD can is implanted in the left pectoral region and used as an electrode. This position, along with an electrode in the right ventricle, yields a current vector that transverses the critical areas of the heart.

The ICD can makes a suitable electrode because of its large surface area. However, known designs still do not provide optimal electrode function. Known cans are constructed of titanium or stainless steel. The unidirectional current flow from these cans causes the titanium to oxidize, thereby increasing impedance and allowing plating of metal frown one electrode to the other. This permits an unacceptably large potential for change of original electrode characteristics.

Future devices will undoubtedly be smaller and deliver less energy. It is therefore desirable to optimize the performance of the can as an electrode. The can material cannot easily be changed to a different material with better electrode properties because the characteristics that make the can suitable as an electrode may make it unsuitable for use as a structural element, for example its function as a hermetic sealing element and as an EMI barrier.

The present invention involves coating the entire ICD can, or in the alternative, predetermined portions of the can, with a coating to reduce the effects of oxidation of the can material over a time period with multiple shocks. Oxidation of the can may cause changes in the impedance, polarization and appearance of the can. The coating comprises a noble metal based substance. The coating preferably comprises platinum Platinum coating has been demonstrated to give superior electrode performance compared to prior an titanium and stainless steel. The coating may be accomplished by plating, vapor deposition, cladding, or welding. The can may be completely coated. Alternatively, selected areas may be coated, either in a pattern, such as a grid, or continuously. Selective coating is desirable in a can design where two can parts are welded together so that the coating doesn't interfere with the welding process. Such interference may cause poor welds or create new alloys at the weld seam that may promote corrosion.

A primary aspect of the present invention is to use the PG-housing electrode both in lieu of the subcutaneous-patch electrode and as an augmentation to it, providing either two, three, or four electrodes. Both cases permit a variety of pulse-sequence and pulse-axis combinations, with the second term referring to the spatial direction of the discharge, fixed by polarity and electrode choices.

In pectoral implantation of a PG, the entire PG exterior may be employed as an electrode. This provides a large electrode area, and hence a small parasitic contact resistance. While the low contact resistance is a desirable goal, the system could pose a serious shock hazard to medical personnel handling it before and during implantation. Also, this arrangement would not allow steering the current in a desired direction.

Figure 4:
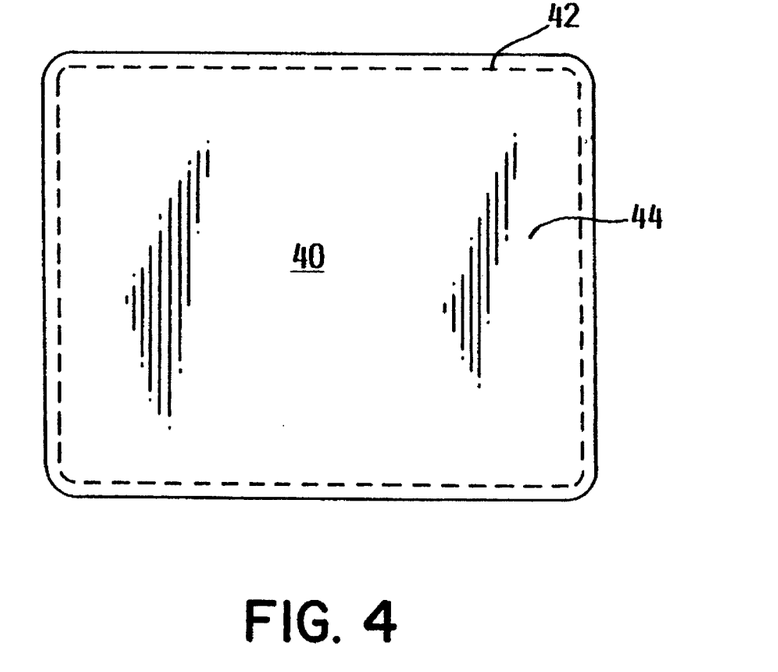
FIGS. 4, 5 and 6 illustrate schematic representations of a defibrillating system of the present invention having a PG housing with one major metallic face exposed to serve as an electrode, and the balance of the PG surface area covered by an insulating layer.
Figure 5:
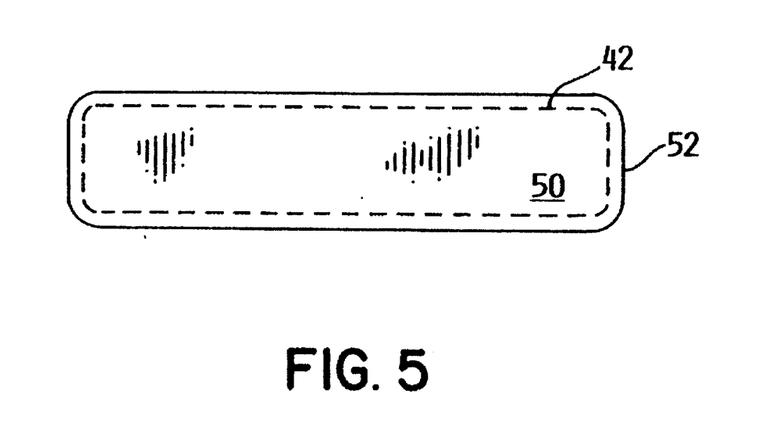
Figure 6:
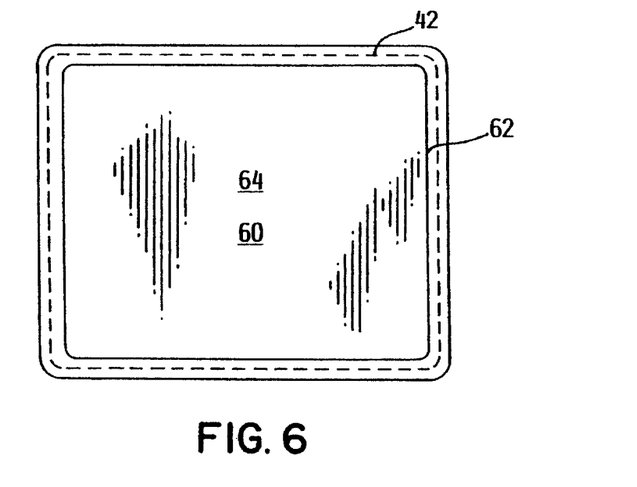

The application of an insulating layer to portions of the PG's external surface largely eliminates tile shock hazard and provides the beneficial result of allowing the current to be steered in a direction most advantageous for defibrillation. The PG housing desirably approximates a somewhat flattened rectangular parallelepiped. This geometry allows most of one major face of the housing to serve as the electrode, with the balance being insulated, as is illustrated in FIGS. 4, 5 and 6. Because the four smallest faces, or edges, as well as one major face, of the PG are insulation-covered, safe handling of the PG is comparatively straightforward and can be accomplished without risk to the surgeon during implantation. A further benefit of this arrangement is that the electrical discharge can be aimed in a chosen direction. For example, aiming the discharge toward the interior of the body causes primary current conduction to avoid the skin, which largely avoids the additional discomfort normally accompanying and electrode not in direct contact with the heart. On the other, hand, aiming the discharge away from the interior of the body causes the path length, and hence parasitic resistance, to increase, but causes less skeletal muscle "jerk". By this is meant a reflexive contraction of skeletal muscles in tile path of the electrical discharge, and stimulated by it, with uncomfortable, and possibly injurious results.

Figure 7:
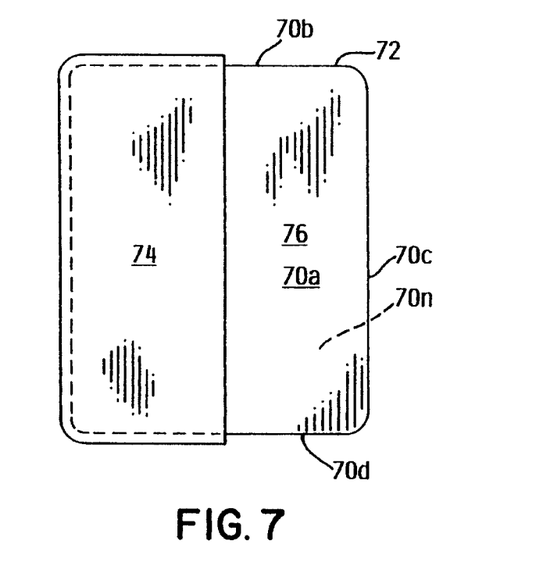
FIGS. 7 and 8 illustrate schematic representations of a defibrillating system of the present invention having a PG housing with approximately half its surface-area exposed to serve as an electrode and the balance of the PG surface area covered by an insulating layer.
Figure 8:
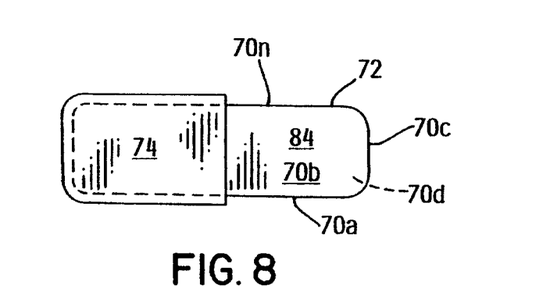

As a further option, another portion of the PG housing could be covered with an insulating coating, as shown in FIGS. 7 and 8. The ease and safety of handling of this configuration approximates that for the preceding option, but additionally provides a wider range of aiming options due to the increased number of surfaces which are not insulated.

Figure 9:
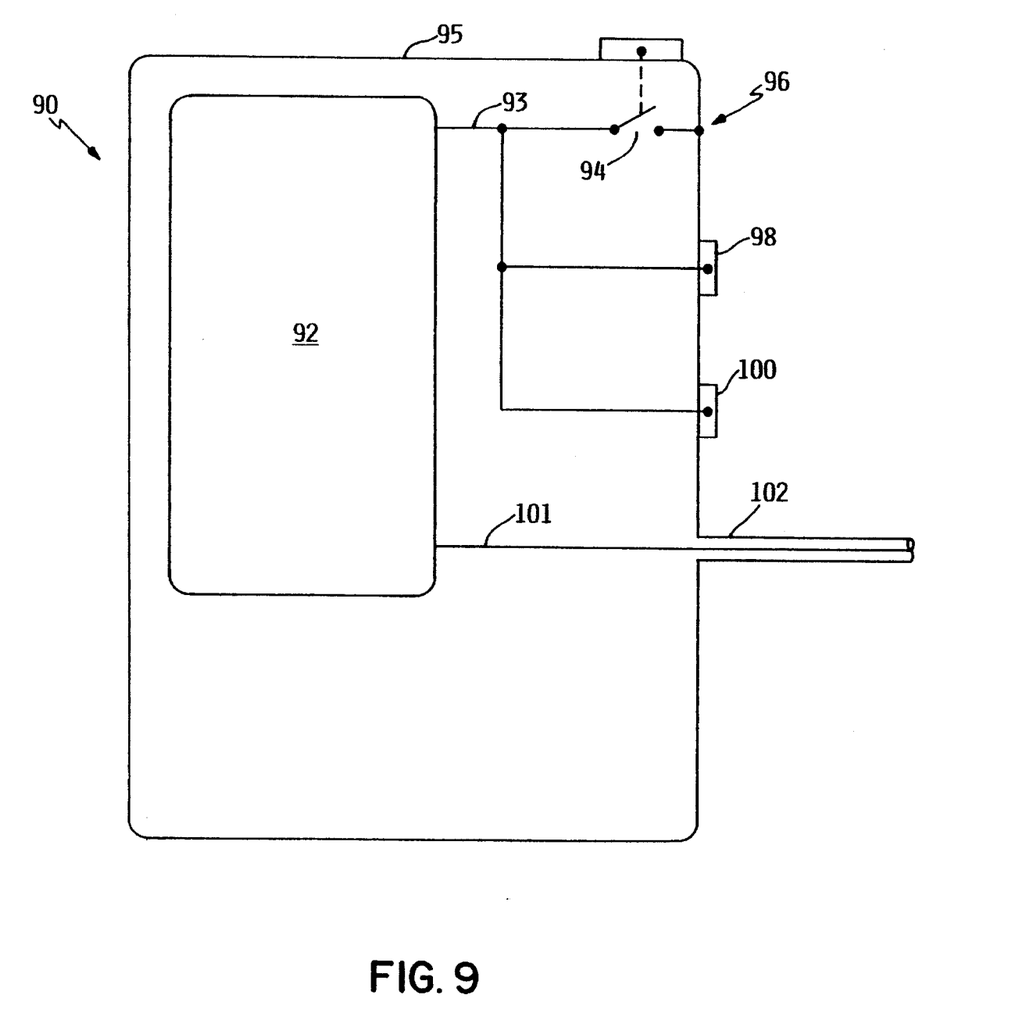
FIG. 9 illustrates a schematic representation of a defibrillating system of the present invention incorporating a selector switch that permits the PG to serve either in the PG-housing-as-electrode mode or in other conventional modes.

While tile conductive PG housing will be most advantageously used in the pectoral implant, it can also be used in conventional abdominal implantation by adding a single-pole, single-throw selector switch to the system, as shown in FIG. 9. When selector switch 94 is open, as in FIG. 9, the metal housing of the PG is isolated from all circuitry, and tile PG may be conventionally implanted in the abdominal cavity. But when selector switch 94 is closed, the PG housing is activated as the CAN electrode. By the simple act of plugging in the lead from a SUB electrode, and/or an RA electrode, tile surgeon can realize various electrode-pattern options to accompany the pectorally implanted CAN electrode.

Figure 10:
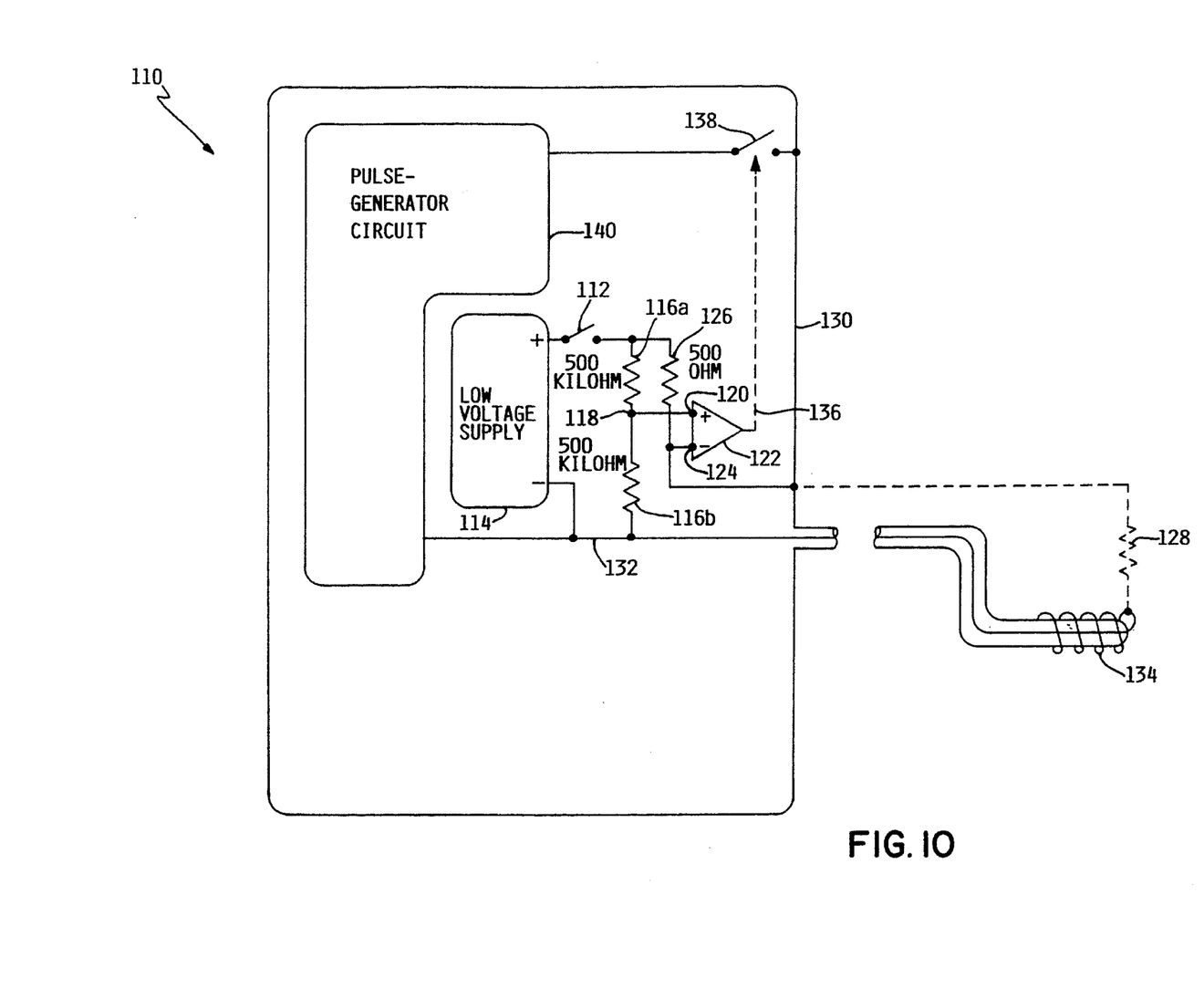
FIG. 10 illustrates a schematic representation of a defibrillating system of the present invention incorporating one possible safety circuit that disables the pulse generator when the housing-to-circuit-common resistance is higher than that encountered by the system after implantation, thus protecting medical personnel who must handle the system before and during implantation.

In the event that further protection against shock is desired, this invention provides a circuit, shown in FIG. 10, for sensing that the implantation procedure has not yet been performed and develops a disabling signal to prevent inadvertent generation of the defibrillation signal. This feature totally eliminates tile shock hazard to medical personnel. It can be viewed as a safety element that augments the exterior insulation described above.

It is evident that combining the PG-housing or CAN electrode with the well-established defibrillation electrodes SVC and RVA, that are often associated with a cardiac catheter, makes possible a number of polarity patterns for applying defibrillation pulses. Beyond this, is the choice of the monophasic pulse pictured in FIG. 11, the biphasic pulse in FIG. 12, and the sequential pulses in FIG. 13. Let it be said that the two pulses in the biphasic waveform, as well as in the sequential waveform are of comparable amplitude and duration, thus avoiding the infinite possible waveform variations. Let "comparable" be taken to mean "within a factor of four".

Consider first the monophasic pulse. Taking the three electrodes in sequence P-VA, SVC, and CAN, FIG. 14 identifies four polarity patterns that are useful. The number in the left-hand column identifies the pattern. The plus and minus symbols indicate the relative polarities of the respective electrodes during discharge, and the zero symbol means that the circuit to the corresponding electrode is open, or else that the electrode is otherwise omitted from the systems. It will be seen that options assigning a zero to the RVA electrode are omitted, because the RVA electrode plays a dominant role in directing current through the bulk of the left-ventricular muscle. Furthermore, it has been found that assigning the same polarity to the RVA and SVC electrodes, that is, making them electrically common, is an ineffective option. Note that simple polarity reversal has been treated as a separate pattern. That is, pattern 3 is the reverse of 1, and 4 is the reverse of 2. Finally, the case with the CAN electrode open or removed is omitted because it reverts to the prior art.

Figure 12:
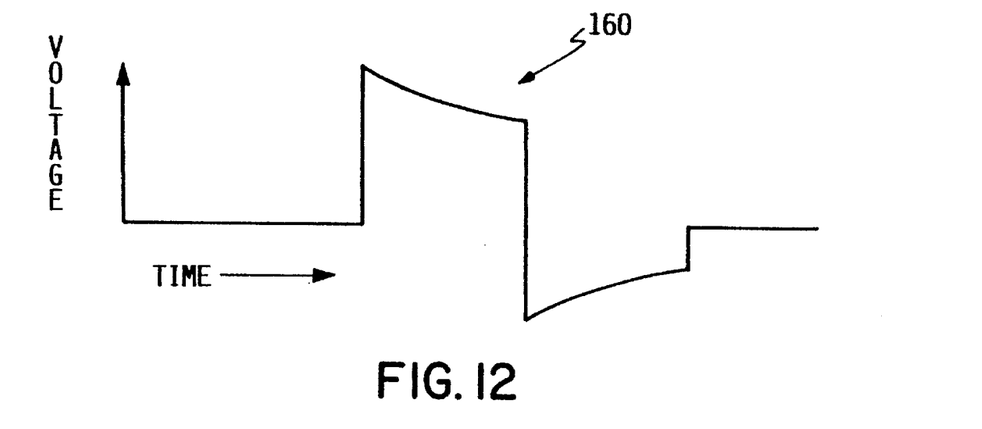
FIG. 12 illustrates a biphasic waveform that in the present invention is applied to a novel set of electrodes in novel patterns.
Figure 13:
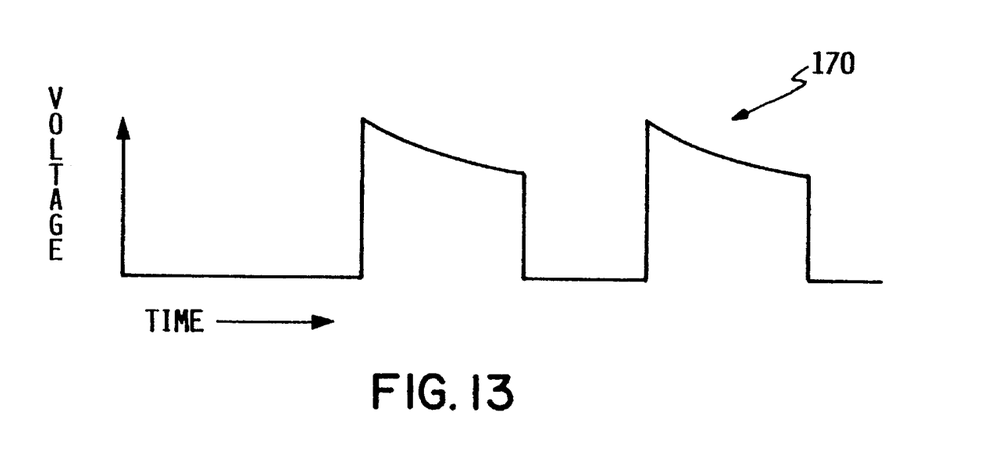
FIG. 13 illustrates a sequential-pulse waveform that in the present invention is applied to a novel set of electrodes in novel patterns.
Figure 14:
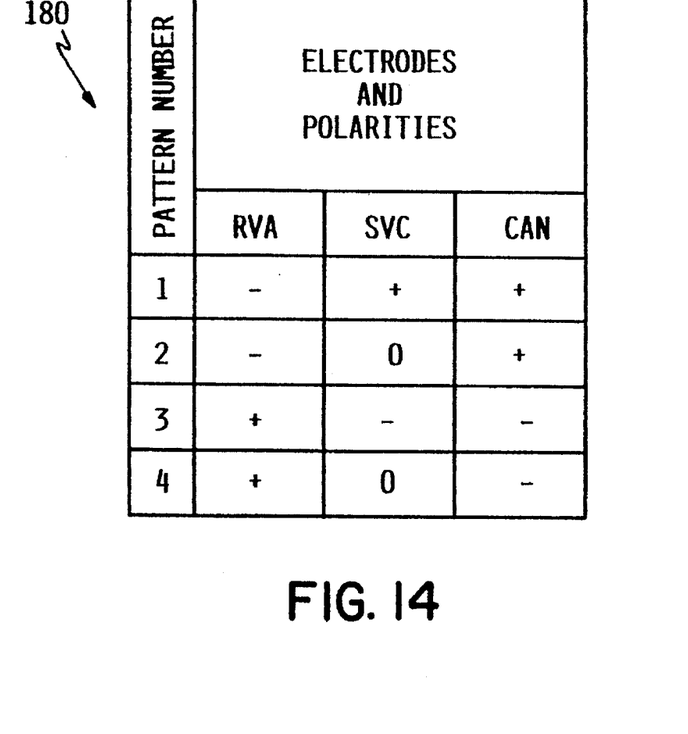
FIG. 14 illustrates a chart of useful polarity patterns for three electrodes, RVA, SVC and CAN, describing the cases of monophasic and first-biphasic-pulse waveforms.

Next, the four patterns in FIG. 14 may be interpreted as a description of the first pulse in the biphasic waveform of FIG. 12. Thus, FIG. 14 deals fully with both the monophasic and biphasic cases. The case of two pulses in sequence involves additional considerations. First, identify a given sequential-pulse option by using tile pattern identification numbers. Thus, "12" would mean that tile first pulse is of pattern 1, and the second, pattern 2. It has been found that two same-pattern ( and otherwise similar) pulses in a sequence are not beneficial. In tile sequential-pulse representation of FIG. 13, different polarity patterns are assumed for the two pulses. Therefore, tile sequence options 11, 22, 33 and 44 are dropped from consideration. Next, a sequence involving simple polarity inversion on all electrodes in going form the first pulse to the second is also omitted because this simply constitutes one of the biphasic options. This removes 13, 31, 24 and 42. Next, consider that a pattern eliminating the RVA electrode may be useful as one of the two sequential pulses, even though it is not useful in the monophasic case. There are two such patterns given in FIG. 15, and numbered 5 and 6. Thus, it is possible to list exhaustively all useful pattern combinations in the sequential case, as has been done in FIG. 16.

Figure 16:
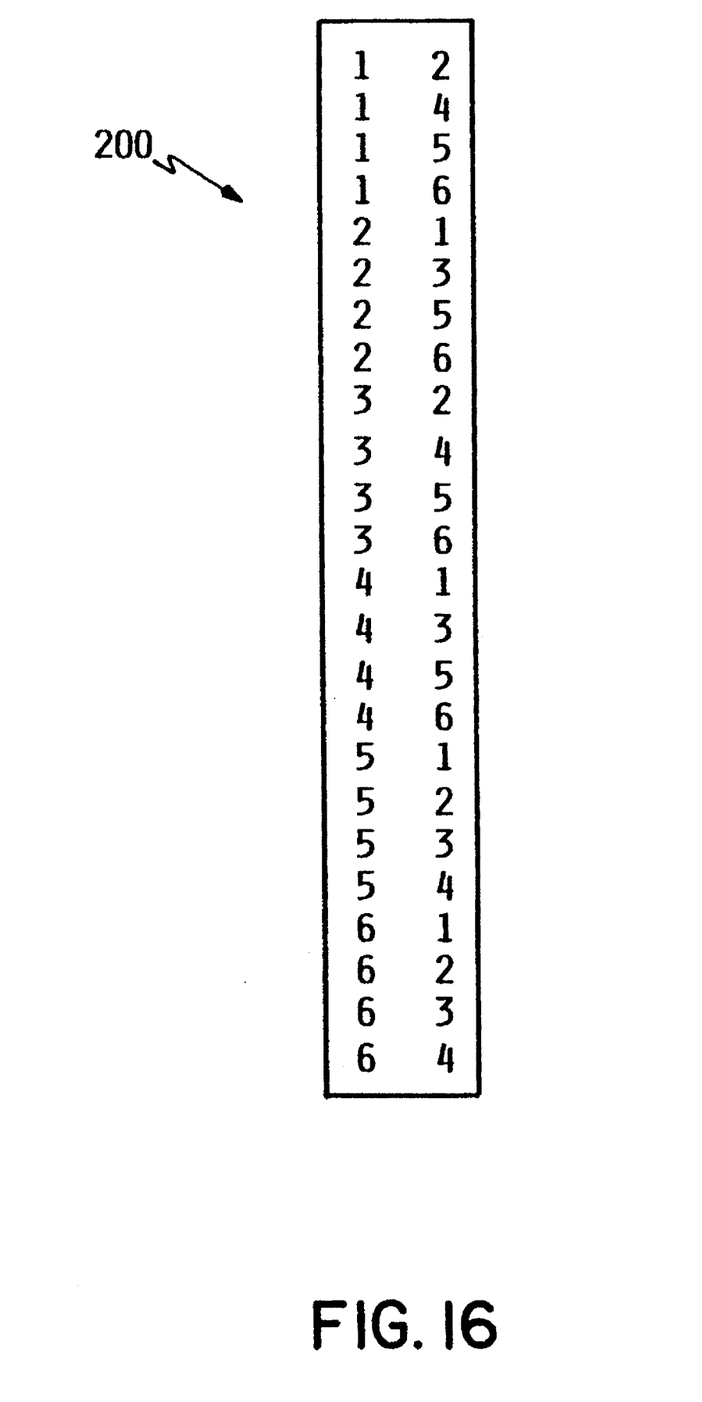
FIG. 16 illustrates a chart of three- and four-electrode pattern combinations useful in sequential-pulse defibrillation.
Figure 17:
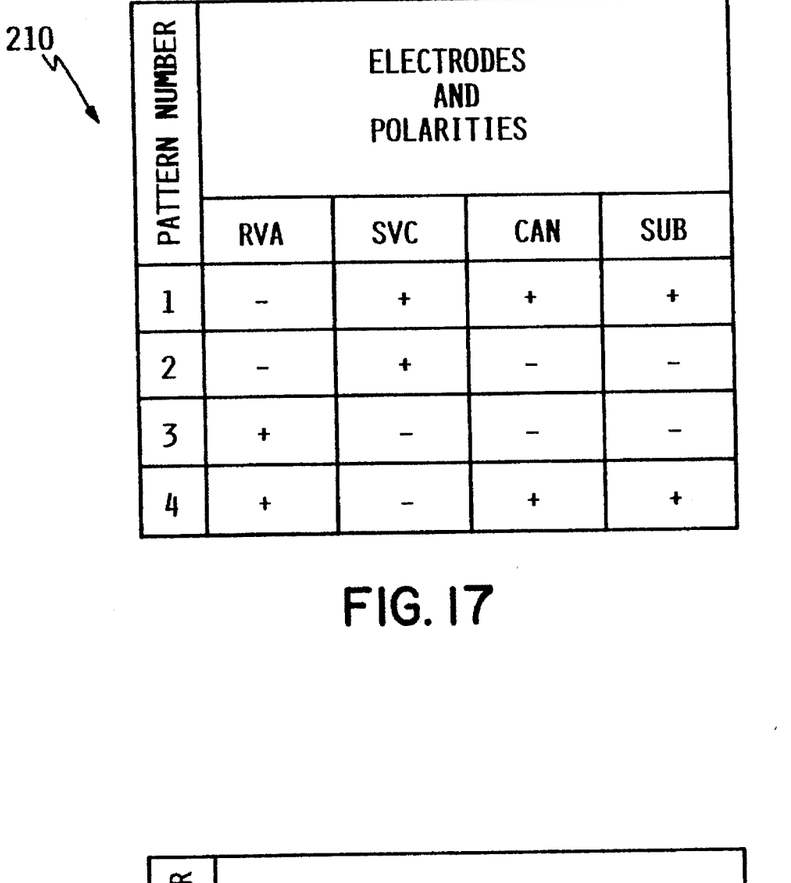
FIG. 17 illustrates a chart of useful polarity patterns for four electrodes, RVA, SVC, CAN and SUB, for the cases of monophasic and first-biphasic-pulse waveforms.
Figure 18:
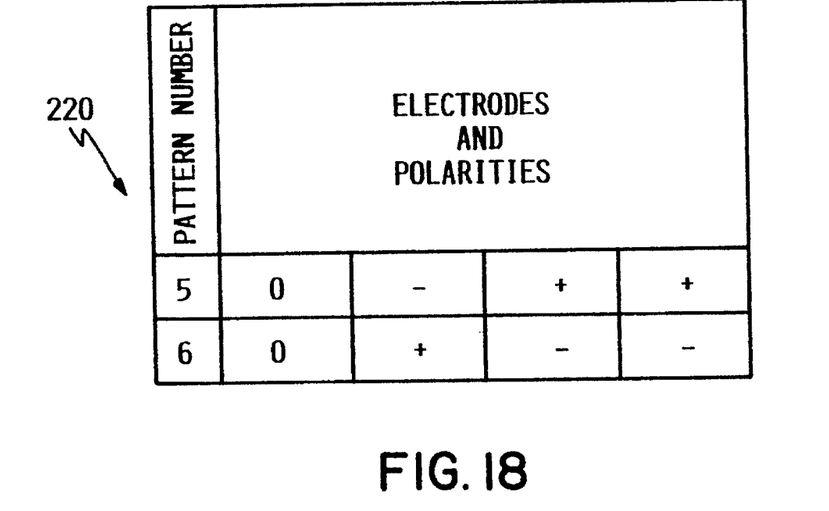
FIG. 18 illustrates a chart of additional polarity patterns for use in sequential-pulse waveforms in the four-electrode case.

When a subcutaneous-patch or SUB electrode is present in addition to the RVA, SVC, and CAN electrodes, the list of patterns must be reconsidered. Once again, a pattern with RVA and SVC common is rejected for the same reason as before. Further a pattern with CAN and SUB having opposite polarities is rejected because the current from one to the other would be remote from the heart and wasted. In addition, a pattern with CAN open is avoided because it constitutes prior art, and a pattern with SUB open is also avoided because such cases have already been treated in FIGS. 14, 15 and 16. Thus, there are four patterns again this time, as given in FIG. 17. Again, there are two additional patterns that are potentially useful in the sequential case, as given in FIG. 18. Because the symmetries in FIGS. 17 and 18 are identical to those in FIGS. 14 and i 5, it follows that FIG. 16 give the useful pattern combinations for the case of four electrodes, as well as for the case of three electrodes.

FIG. 1 illustrates a schematic drawing of a patient 10 fitted with a defibrillating system of the prior art consisting of a PG 12 implanted in the abdominal cavity and connected to epicardial-patch electrodes 14 and 16 by electrical-lead harness 18.

FIG. 2 illustrates a schematic drawing of a patient 20 fitted with a defibrillating system of the prior art consisting of a PG 22 implanted in the abdominal cavity and connected to transvenous RVA electrode 24 and subcutaneous-patch electrode 26 by means of electrical-lead harness 28 where all numerals correspond to those elements previously described.

FIG. 3 illustrates a schematic drawing of a patient 30 fitted with a defibrillating system of the present invention comprising a pectorally implanted PG 32, a subcutaneous-patch electrode 34, and transvenous catheter 36, carrying an SVC electrode 38, and an RVA electrode 39 where all numerals correspond to those elements previously described.

FIG. 4 illustrates the top face 40 of a PG 42 having an insulating layer 44 that covers the entire top surface of the PG exterior where all numerals correspond to those elements previously described.

FIG. 5 illustrates an elevation of a PG 42 having an insulating layer 52 that covers the entire surface of the face 50 depicted, and also covers the remaining three "edge" faces where all numerals correspond to those elements previously described.

FIG. 6 illustrates the bottom face 60 of the PG 42 having an insulating layer 62 that covers only the periphery of the bottom major face 60, leaving the balance 64 of the bottom face 60 within the periphery of the insulating layer 62 to serve as an exposed-metal electrode.

FIG. 7 illustrates a side view of a PG 72, including a plurality of faces 70a–70n, having an insulating layer 74 that covers a significant fraction of the exterior surface of the PG 72, leaving the balance 76 consisting of faces 70a–70n of the exterior surface of the PG 72 in the form of exposed metal to serve as an electrode.

FIG. 8 illustrates a top view of the PG 72 and the insulating layer 74 that covers a significant fraction of the faces 70a–70n, leaving the balance 84 consisting of faces 70a–70n in the form of exposed metal to serve as an electrode.

FIG. 9 illustrates a PG module 90 and represents schematically certain of its internal elements that permit flexible application of the system where all numerals correspond to those elements previously described. The pulse-generator circuit 92 has a first output lead 93 connected through the externally controlled SPST selector switch 94 to the PG housing 95 at the connection point 96. When the switch 94 is open, the PG module 92 can be abdominally implanted in conventional fashion; when the switch 94 is closed, the PG housing 95 can be employed as a defibrillation electrode in the case of pectoral implantation. The first output lead 93 is also connected to a first self-sealing output jack 98 into which an SVC electrode lead can be plugged when desired, as well as to a second self-sealing output jack 100 into which a SUB electrode can be plugged when desired. A second output lead 10 1 from the pulse-generator circuit 92 is permanently connected inside a lead 102 that is intravenously installed to place an electrode in the RVA position. Activation of an SVC electrode is accomplished by plugging its lead into jack 98, and activation of a SUB electrode is accomplished by plugging its lead into jack 100. With these options, in addition to that provided by selector switch 94, it is evident that the flexibility of the present invention offers the choice of three single-electrode options, of three common-double-electrode options, and one common-triple-electrode option, for a total of seven options for an electrode pattern to deliver a shock directed at the opposing RVA electrode that is connected to the pulse-generator circuit 92 through the lead 102.

FIG. 10 illustrates a PG module 110 that incorporates a safety circuit for disabling the pulse generator until the system has been implanted where all numerals correspond to those elements previously described. The safety circuit senses when the system has been implanted by monitoring the resistance between the implanted RVA electrode 134 and the metal housing 130 of the system. When the resistance drops to a low level, the system develops a signal that allows defibrillation pulse to be passed to the CAN or PG-housing electrode.

When the pulse generator 140 is prepared to deliver its pulse or other waveform it closes SPST switch 112 by conventional circuit means. Closing SPST switch 112 causes current from low-voltage power supply 114 to flow through a center-tapped 1-megaohm resistor, that is through resistors 116a and 116b. This creates a reference voltage, having a value one half that of the output from the low-voltage supply 114, to be developed across resistor 116a, and causes the centertap 118 to become a reference terminal.

The reference voltage at the centertap 118 is fed to a first, positive, input terminal 120 of comparator 122. A "test" voltage, responsive to the resistance between the CAN electrode metal housing 130 and the RVA electrode 134 is applied to a second, negative, input terminal 124 of comparator 122. This voltage is derived from a voltage divider consisting of a 500-ohm resistor 126 as the "upper" element, and as the "lower" element, the resistance 128 existing at that time from the metal housing of the PG or CAN electrode 130 to the common terminal 132 of the high- and low-voltage circuits, which is also common to the RVA electrode 134. It will be appreciated that, while FIG. 10 illustrates the resistance between the CAN electrode 130 and the RVA electrode 134 as a resistor 128 shown in dotted lines, in actuality, the resistance is not a discrete resistor, but rather the resistance of the path that exists at the time between these electrodes. Before the device is implanted, the path will be largely air and have a very high resistance. However, after implantation, the path will be through relatively highly conductive body tissue, and therefore, have a relatively low resistance.

Even when a person is handling the system, and holding the metal housing of the system in one hand and the RVA electrode in the other, the resistance between circuit points 130 and 134 (from hand to hand) is typically several kilohms, so that the test voltage at negative input terminal 124 is much more positive than the reference voltage at positive input terminal 120, so that the comparator delivers a logical "low", or zero voltage at output terminal 136. This output signal controls the switch 138, and zero voltage to that switch, which is preferably an FET, meaning that the switch is inactivated and hence open. With switch 138 open, the defibrillation pulses from pulse generator 140 are blocked and do not reach the CAN or housing electrode 130.

When the PG module 110 is properly implanted, the electrical path represented by the resistor 128 from the housing electrode 130 to the RVA electrode 134 will lie through body tissue and have a resistance value well below 500 ohms, causing the reference voltage at positive input terminal 120 to be more positive than the test voltage at negative input terminal 124, causing the comparator to switch to the logical "high" condition at output terminal 136. This high signal at comparator output terminal 136 causes switch 138 to close, thereby permitting the normal delivery of the defibrillation pulses from pulse generator 140 to the metal housing 130.

The safety circuit operates for all CAN electrode 130 configurations without modification and functions to prevent accidental shock regardless of the selected pulse polarity. Thus, the medical team is protected in all situations where the shock hazard is present and the safety feature imposes no limitations on the electrode selection, the choice of pulse polarity, or other options such as the pulse sequence or waveform. Further, it is evident that the PG module 110 and its circuitry of FIG. 10 can be combined with the PG module 90 and its circuitry of FIG. 9 by combining the switches 138 and 94 into one switch operable by either of two means.

Figure 11:
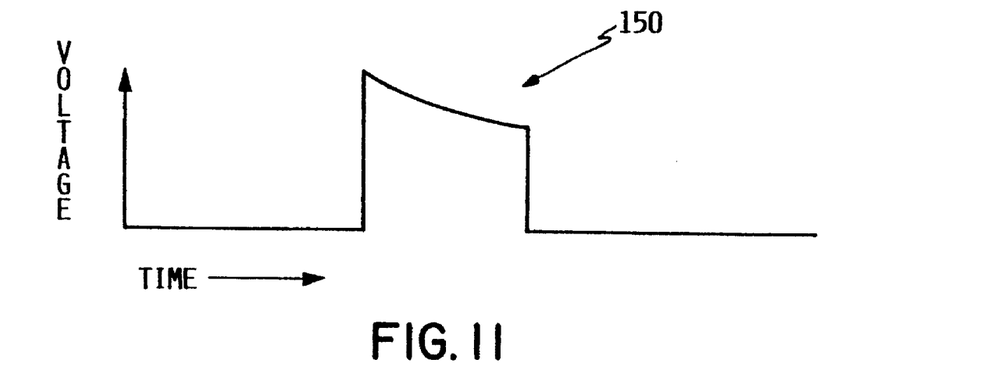
FIG. 11 illustrates a monophasic waveform that in the present invention is applied to a novel set of electrodes in novel patterns.

FIG. 11 illustrates a defibrillation waveform 150 known in the prior art as monophasic that hi tile present invention is applied to a novel set of electrodes in novel patterns.

FIG. 12 illustrates a defibrillation waveform 160 known in the prior art as biphasic that in the present invention is applied to a novel set of electrodes in novel patterns.

FIG. 13 illustrates a defibrillation waveform 170 comprising a pair of sequential pulses that in the present invention is applied to a novel set of electrodes in novel patterns.

FIG. 14 illustrates a chart set 180 of useful polarity patterns for defibrillation using three electrodes: right-ventricular apex (RVA); superior vena cava (SVC); and PG housing (CAN). The set 180 omits patterns that have been found ineffective. The plus and minus symbols indicate relative polarities of the respective electrodes during discharge, and the zero symbol means that the circuit to the corresponding electrode is open, or that the corresponding electrode is otherwise removed form the system. The set 180 is applicable to a monophasic waveform, and to the initial pulse of a biphasic waveform.

Figure 15:
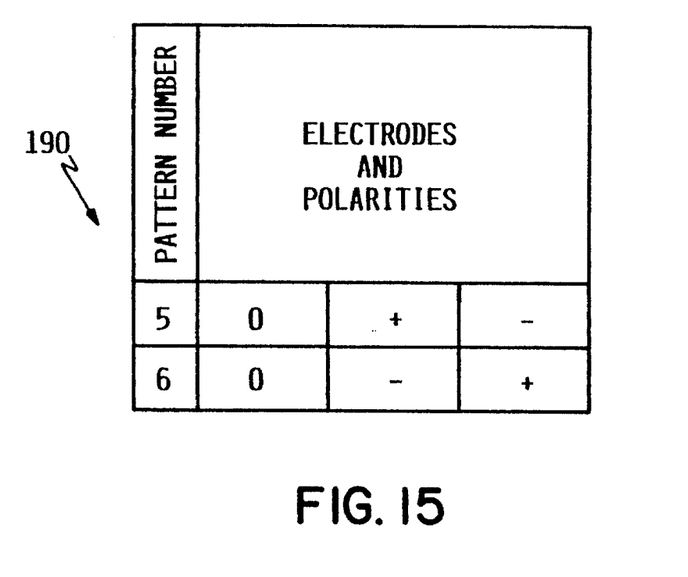
FIG. 15 illustrates a chart of additional polarity patterns for use in sequential-pulse waveforms in the three-electrode case.

FIG. 15 illustrates a chart set 190 of additional polarity patterns for defibrillation using the RVA, SVC and CAN electrode patterns that are for use in one of the pulses in a two-pulse sequential waveform.

FIG. 16 illustrates a chart set 200 of twenty-four pattern combinations for use in sequential-pulse defibrillation. Each digit in the chart refers to the corresponding polarity pattern defined in FIGS. 14 and 15, and each pair of digits represents a sequential-pulse option for two pulses in the case of three electrodes as in FIGS. 14 and 15, and for the case of four electrodes as in FIGS. 17 and 18 which follow.

FIG. 17 illustrates a chart set 210 of useful polarity patterns for defibrillation using the RVA, SVC, CAN and SUB (subcutaneous-patch) electrodes. The set 210 omits patterns that are know to be ineffective, and is applicable to a monophasic waveform, and to the initial pulse of a biphasic waveform.

FIG. 18 illustrates a chart set 220 of additional polarity patterns for defibrillation using the RVA, SVC, CAN and SUB electrodes, patterns that are for use in one of the pulses in the two-pulse sequential waveform.

As many changes are possible to the embodiments of this invention utilizing the teachings thereof, the descriptions above, and the accompanying drawings should be interpreted in the illustrative and not the limited sense.

The invention claimed is:

1. An implantable cardioverter defibrillator system comprising a pulse generator, a lead connecting said pulse generator to a first electrode whereby an electrical pulse generated by said pulse generator is conducted to said first electrode, a second electrode, said second electrode comprising an external area of said pulse generator, said external area being in electrical contact with pulse generation circuitry of said pulse generator wherein a pulse generated through said first electrode is discharged against said second electrode, said external area being coated with an oxidation resistant material.

2. The system of claim 1, further comprising electrical insulation material coveting selected areas of said pulse generator.

3. The system of claim 1, further comprising a third electrode and lead therefor, said third electrode connected to said pulse generator by said lead and being dischargeable against said second electrode.

4. The system of claim 3, wherein said third electrode is a patch electrode.

5. The system of claim 4, wherein said patch electrode is a subcutaneous patch electrode.

6. The system of claim 3 wherein said first and third electrodes are transvenous electrodes.

7. The system of claim 3 wherein said system further comprises a transvenous catheter carrying said first and third electrodes, said catheter being in electrical connection with said pulse generator.

8. The system of claim 1, wherein said pulse generator is implanted subcutaneously in the left pectoral region of a patient.

9. The system of claim 1, wherein said second electrode is aimed inwardly into a patient's body towards the heart.

10. The system of claim 1, wherein said oxidation resistant coating material comprises a noble metal.

11. The system of claim 10, wherein said noble metal is platinum.

\* \* \* \* \*